United States Patent
Fykes-Morgan

(10) Patent No.: US 12,256,869 B2
(45) Date of Patent: Mar. 25, 2025

(54) TOUCH-LESS AUTOMATIC CONDIMENT DISPENSER

(71) Applicant: Kyli Fykes-Morgan, Indianapolis, IN (US)

(72) Inventor: Kyli Fykes-Morgan, Indianapolis, IN (US)

( * ) Notice: Subject to any disclaimer, the term of this patent is extended or adjusted under 35 U.S.C. 154(b) by 378 days.

(21) Appl. No.: 17/391,225

(22) Filed: Aug. 2, 2021

(65) Prior Publication Data

US 2023/0030100 A1 Feb. 2, 2023

(51) Int. Cl.
*A47J 47/01* (2006.01)
*A61L 2/10* (2006.01)

(52) U.S. Cl.
CPC .............. *A47J 47/01* (2013.01); *A61L 2/10* (2013.01); *A61L 2202/11* (2013.01)

(58) Field of Classification Search
CPC ..... B05C 5/001; B05C 11/1042; B65D 83/72; B67D 1/0857; B67D 3/0009; B67D 3/0022; B67D 7/80; B67D 1/0888; A47J 31/60
USPC ................................. 222/20, 14, 16, 52, 129
See application file for complete search history.

(56) References Cited

U.S. PATENT DOCUMENTS

| | | | |
|---|---|---|---|
| 1,947,364 A * | 2/1934 | Spino ..................... | A47F 1/035 312/61 |
| 6,269,980 B1 * | 8/2001 | Randall ................ | B67D 3/0029 222/481.5 |
| 6,814,262 B1 * | 11/2004 | Adams ................... | A23G 9/283 417/478 |
| 7,595,470 B1 * | 9/2009 | Sizer ..................... | H05B 6/802 219/689 |
| 7,909,209 B2 | 3/2011 | Reynolds | |
| 8,950,628 B2 * | 2/2015 | Muderlak ............ | A47K 5/1217 222/25 |
| 9,809,439 B2 | 11/2017 | Falco, III | |
| 2012/0223098 A1 | 9/2012 | Natterer | |
| 2013/0264355 A1 | 10/2013 | Jodoin | |
| 2014/0203039 A1 * | 7/2014 | Maas ..................... | B05C 17/002 222/52 |
| 2020/0282414 A1 * | 9/2020 | Gauger ................... | G07F 13/06 |
| 2021/0047165 A1 * | 2/2021 | Showalter ........... | B67D 1/0802 |
| 2021/0383084 A1 * | 12/2021 | Johnson ............ | G06K 7/10237 |
| 2022/0033242 A1 * | 2/2022 | Zubarik ................. | G07F 13/06 |

* cited by examiner

*Primary Examiner* — Vishal Pancholi
*Assistant Examiner* — Robert K Nichols, II

(57) ABSTRACT

A touch-less, hands-free, automatic condiment dispenser which allows a user, through a mobile app interface, to dispense specific volumes of individual condiments. The automatic condiment dispenser includes UV LEDs for sanitation of the apparatus and temperature control for maintaining condiments at specific temperatures.

18 Claims, 4 Drawing Sheets

TOUCH-LESS AUTOMATIC CONDIMENT DISPENSER

CROSS-REFERENCES TO RELATED APPLICATIONS

This application claims the benefit of provisional application No. 63/066,292 entitled TOUCH-LESS AUTOMATIC CONDIMENT DISPENSER, filed Aug. 16, 2020. The provisional application is incorporated in its entirety by reference.

FIELD OF INVENTION

One or more embodiments of the present invention relate to a hands-free, touch-less automatic apparatus for dispensing of condiments. In particular, the invention relates to an apparatus incorporating motion sensors which allow for the hands-free dispensing of condiments and methods for use thereof.

BACKGROUND OF THE INVENTION

The recent coronavirus pandemic has brought renewed interest and increased innovation in areas that have previously been taken for granted. The rapid spread of microbial pathogens, including the novel coronavirus, has been attributed to person-to-person transmission. Respiratory droplets that are produced when an infected person breathes heavily, coughs, or sneezes can land in the noses or mouths of person that are within a 6-foot radius. These respiratory droplets may also land on solid surfaces and be picked up by the hand of a person which can subsequently be transferred to the nose or mouth. Certain areas of high traffic may be more susceptible to respiratory droplet transmission in this manner.

"Condiments" are edible substances that are routinely added to foods to enhance taste. Examples of condiments are ketchup, mustard, mayonnaise, pickle relish, dressings, and sauces. Condiments are typically packaged in containers that requires the user to physically manipulate the container in order to dispense the desired amount. Conventional condiment containers include single-use and multiple use packets, bottles, jars, squeeze-bottles, pump-style dispensers, dipper-style containers, and counter-top dispensers. Many conventional condiment containers are used in high traffic areas, including restaurants, sporting venues, bars, and other entertainment establishments. The sharing of single-use and multiple use condiment dispensers may increase the spread of microbial pathogens through hand to nose or mouth transmission. Multiple users operating traditional pump-style, or dipper style containers among others may inadvertently contribute to the spread of respiratory droplets containing microbial pathogens.

Conventional condiment dispensers also typically provide inconsistent amounts of the condiment. Users are left to determine what level of force is required to dispense a small or large amount of the condiment. This routinely results in spillage of condiments and waste, leading to excess costs for business owners.

Further, conventional condiment dispensers rely on valves or pumps that can retain residual condiment in difficult to clean areas resulting in bacterial and microbial pathogen proliferation. The only way to effectively eliminate microbial pathogen presence in these dispensers is to complete disassembly and physically disinfect individual parts.

Touch-less dispensers for soaps and cleaning products are currently marketed and available for sale. These touch-less dispensers are not suitable for the storage and dispensing of food condiments and are difficult if not impossible to sanitize. Also, these dispensers are not equipped to be operated by a mobile app and do not incorporate temperature control elements to keep condiments cold, hot or at room temperature. Further, these commercially available dispensers are plagued by failures which result in condiment dumping, i.e., large amounts of unwanted condiment dispensing on food or counter.

Therefore, what is needed is a hands-free, touch-less condiment dispenser that can be operated by a mobile app for condiment selection and dispensing volume; contains elements for condiment heating or cooling; and includes an emergency shut-off valve to prevent condiment dumping.

SUMMARY OF THE INVENTION

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter. The present invention is defined by the claims.

An embodiment of the present invention is a touch-less, hands-free, automatic condiment dispenser which allows a user to dispense specific volumes of individual condiments. Another embodiment of the present invention is a method of using a touch-less, hands-free, automatic condiment dispenser.

BRIEF DESCRIPTION OF THE DRAWINGS

The present invention is described in detail below with reference to the attached drawing figures, wherein.

DETAILED DESCRIPTION OF THE INVENTION

Some embodiments of the present invention are described with specificity herein to meet statutory requirements. However, the scope of the invention is not intended to be defined by the description itself. The claimed subject matter may be embodied as to include different features, elements, components, steps, or combinations of steps, similar to those described herein, and in combination with other existing or future technologies. Moreover, although the term "step" might be used to connote different elements of the methods employed, this term should not be interpreted as implying any particular order among or between various steps herein disclosed unless and except the order of individual steps is explicitly described or required.

Some embodiments of the present invention may comprise an apparatus for holding and dispensing at least one condiment, wherein the apparatus comprises a housing, at least one condiment containing compartment, at least one pumping mechanism, and at least one dispenser, and wherein the apparatus further comprises sensors to allow hands-free operation of the dispensing of condiments by detecting the user's presence. In some embodiments, the pumping mechanism may be configured to pump condiments from the compartments to the dispensers. Embodiments of the present invention provide for multi-condiment usage in the same device.

One having skill in the art will recognize that various sensor technologies may be employed towards this purpose, particularly those sensor technologies that detect fluctuations in electromagnetic waves in particular frequency ranges, including but not limited to radar-based sensors, light-based or photo sensors, passive and/or active infrared sensors, and the like. In some embodiments, the sensors may be positioned such that the presents of a food product under the dispense initiates the pumping of condiments. In other embodiments, the sensors may be positioned such that the user may initiate the release of condiment via a gesture in front of the sensor.

Figure 1:
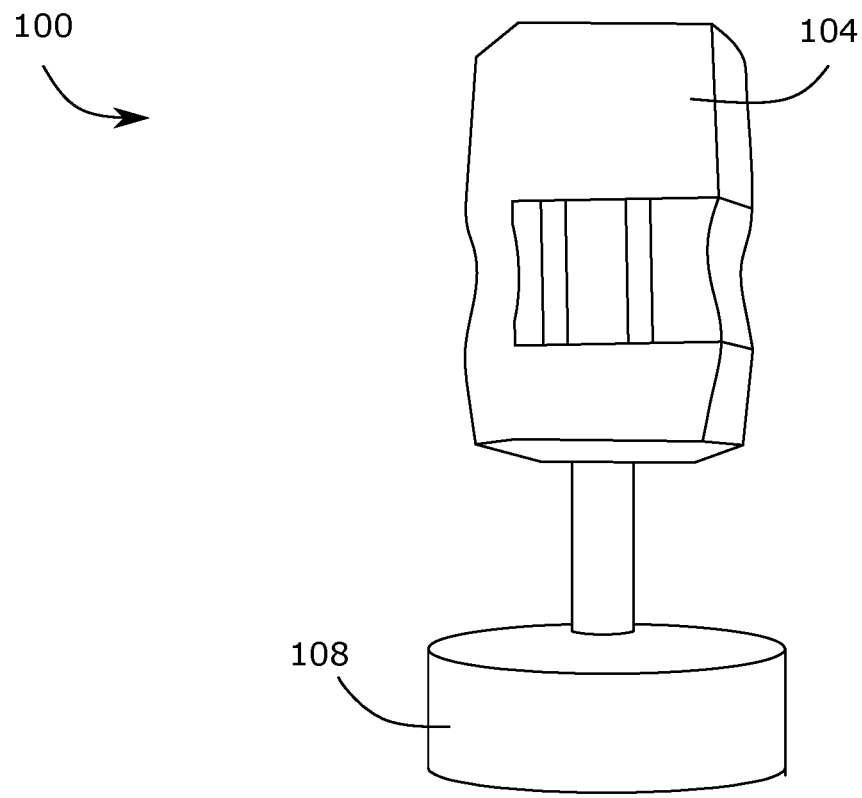
FIG. 1 provides a front view of a countertop embodiment according to aspects of the present invention.

Some embodiments of the present touch-less automatic condiment dispenser may be configured to be placed on a countertop, mounted to a wall, or on a stand. FIG. 1 provides a front view of a countertop embodiment 100 according to aspects of the present invention. As depicted, a housing unit 104 is attached at the top end of a base 108. Condiments are dispensed from below the housing unit 104.

Some embodiments of the present invention may be configured as a space saver model for home use. Such embodiments may provide a handle at the top of the device for easy of movement into and out of the refrigerator and a space-saving profile to better fit on the refrigerator shelf or door compartment.

Figure 2:
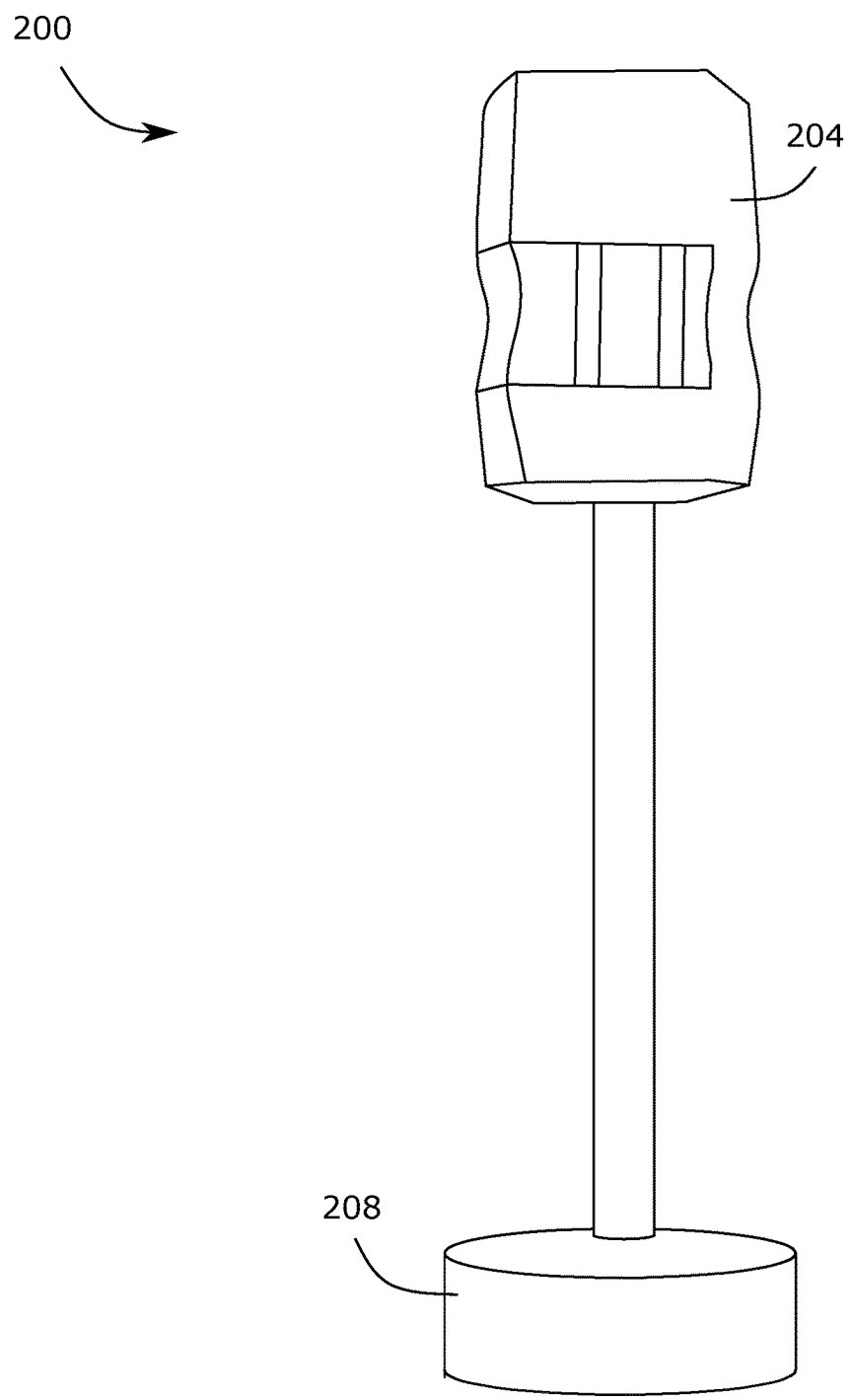
FIG. 2 provides a front view of a stand-mounted embodiment according to aspects of the present invention.

FIG. 2 provides a front view of a stand-mounted embodiment 200 according to aspects of the present invention. As depicted, a housing unit 204 is attached at the top end of a pedestal-style stand 208. Condiments are dispensed from below the housing unit 204.

Figure 3:
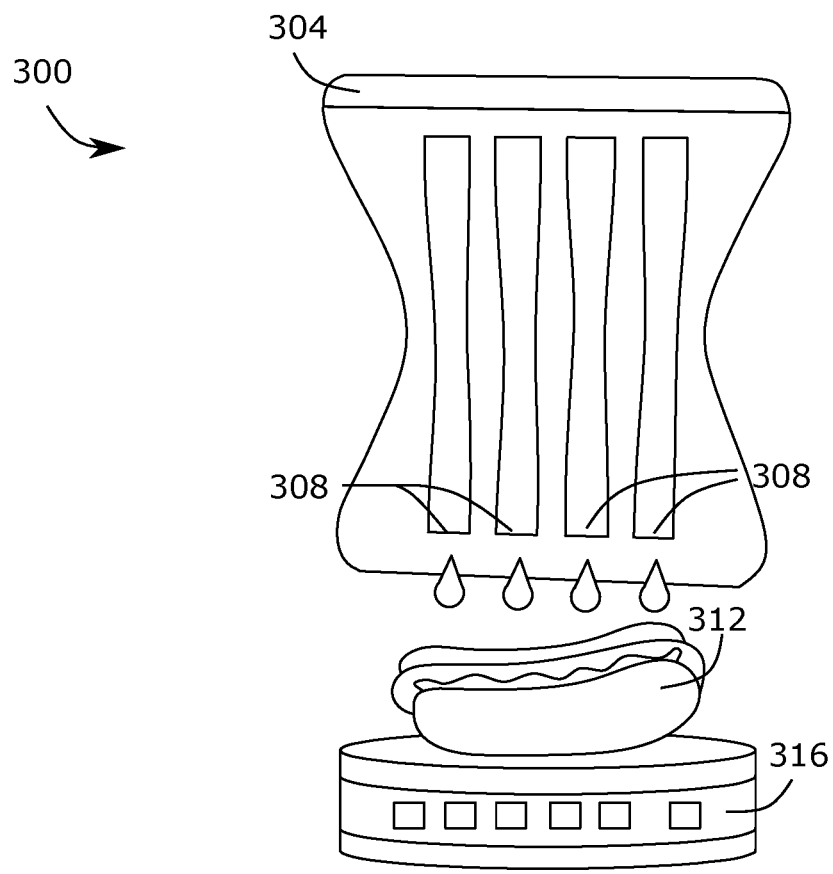
FIG. 3 provide a section view showing inside the housing unit of the touch-less automatic condiment dispenser according to an exemplary embodiment of the present invention.

FIG. 3 provide a section view showing inside the housing unit of the touch-less automatic condiment dispenser 300 according to an exemplary embodiment of the present invention. As depicted, the dispenser comprises a lid 304 that can be opened or removed to insert packages containing condiments. The pumping mechanisms in the apparatus (not shown) pumps condiment out of the packages and through the dispenser outlets 308 and onto the food 312 or into a dish. In some embodiments, the apparatus may also comprise condiment level sensors (not shown) configured to detect the volume of condiment within the condiment containing compartments. The condiment level sensors may also comprise output to indicator lights on the apparatus that indicate when condiment containing compartments volumes are low or empty.

As depicted in FIG. 3, the apparatus further comprises a control panel 316 with mobile app capabilities. The control panel comprises one or more CPUs and/or processors. The mobile app sends signals to the control panel to operate pumping mechanisms to dispense specific amounts of specific condiments. In one or more embodiments of the present touch-less condiment dispenser, the mobile app capabilities include control of the heating and/or cooling elements. The user is able to set specific temperatures for the individual condiment packages within the apparatus from any suitable hand-held device or computer. The mobile app can be installed and operated on any suitable device, including mobile phones, tablets, or laptop computers.

Figure 4:
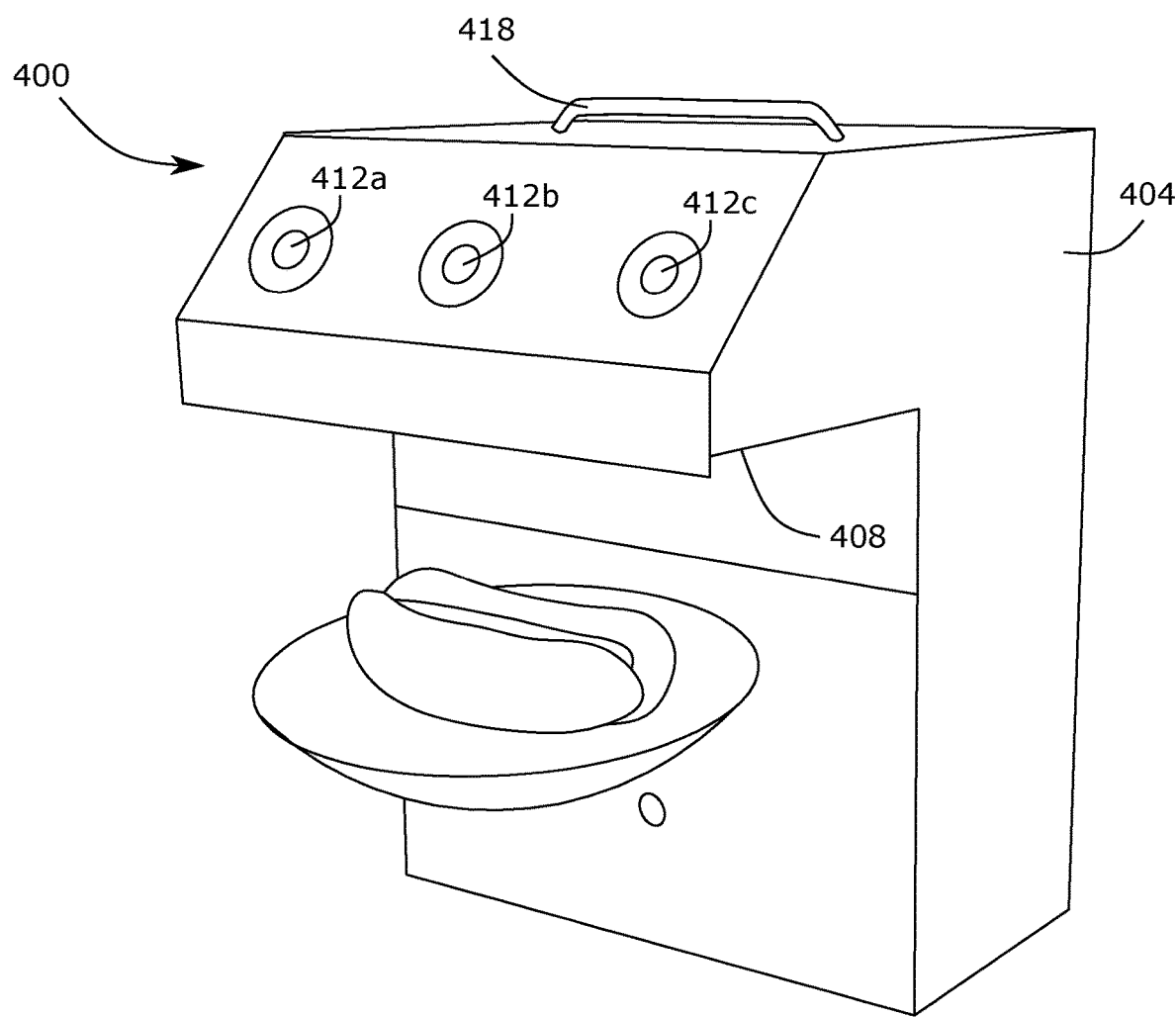
FIG. 4 provides a prospective view of a further embodiment according to aspects of the present invention.

FIG. 4 provides a prospective view 400 of a further embodiment according to aspects of the present invention. The dispenser housing 404, includes an overhang section 408. Condiments may be dispensed from outlet located on the underside of overhang section 408. As depicted, the dispenser is designed to dispense three condiments. Three sensors 412a, 412b, 412c are shown, each corresponding to a separate condiment to be dispensed directly below the sensor. For example, sensor 412a may correspond with mustard such that a user may cause mustard to dispense from directly below sensor 412a by gesturing in front of sensor 412a with a hand.

As depicted in FIG. 4, a handle 418 is included at the top of the dispenser housing 404. This may make the dispenser more portable and, in some embodiments, may make the dispenser easier to move in and out of a refrigerator.

In some embodiments of the present touch-less automatic condiment dispenser, the mobile app can be configured to send an alert message to a user or operator indicating that the contents of a condiment containing compartment is low or empty.

Some embodiments of the touch-less automatic condiment dispenser may also comprise holders for napkins and utensils mounted on the sides of the apparatus.

In some embodiments, the present touch-less automatic condiment dispenser may include a shut off valve on the dispensers. The shut off valves may be configured to prevent condiment dumping and waste if sensors determine that an unusually large amount of condiment has been continually dispensed. The control panel and mobile app include provisions for resetting the shut off valve to continue normal dispensing of condiments.

In some embodiments of the present touch-less automatic condiment dispenser, the apparatus may further comprise heating and/or cooling elements that can be configured to maintain individual condiment packages within the apparatus at specific temperatures. The heating and/or cooling elements can be any suitable commercially available element for maintaining a constant elevated or lowered temperature within the compartment containing the condiment.

In another exemplary embodiment of the present touch-less automatic condiment dispenser, the apparatus contains UV lighting elements for sanitation. The UV lighting elements can be controlled by the mobile app for self-cleaning of the entire apparatus, including the dispensers and pumping mechanisms. The UV lighting elements can be any suitable UV LED configured to emit UV light at a wavelength suitable to kill or disable microbial pathogens.

The present touch-less automatic condiment dispenser can be powered by any suitable power source including an AC power supply or an internal or external battery supply. The present touch-less automatic condiment dispenser is not limited to these power supplies and any other power supply can be used to power the dispenser.

One embodiment of the present touch-less automatic condiment dispenser is a hands-free method for dispensing a specific volume of condiment, which includes the steps of a user inputting commands into a mobile app configured to interface with the control panel of the dispenser, wherein the commands include signals for selecting a specific condiment to be dispensed, and signals for selecting a specific volume of condiment to be dispensed.

In one or more embodiments of the present touch-less automatic condiment dispenser, the apparatus and associated elements can be finished in various colors, including black, and stainless steel. One having skill in the art with recognize that any finish that can be applied to a suitable construction material is possible.

Embodiments of the present invention have been described, as required by statute, to be illustrative, but should not be interpreted to be restrictive. One having skill in the art will recognize that many different arrangements of the various components depicted are possible without departing from the scope of the claims below, as well as arrangements including components not explicitly shown.

One having skill in the art will understand that certain combinations and/or sub-combinations of elements and features are of utility and may be employed without reference to other combinations and/or sub-combinations and are contemplated within the scope of the claims. Not all steps listed in the various figures need be carried out in the specific order described.

What is claimed is:

1. A touch-less automatic condiment dispenser comprising:
    an apparatus configured to hold and dispense at least one condiment;
    wherein the apparatus comprises a housing, at least one condiment containing compartment, at least one pumping mechanism, and at least one dispenser, and wherein the apparatus further comprises:
        at least one sensor to allow hands-free operation of the dispensing of condiments;
        at least one condiment level sensor to allow an indication that the at least one condiment is low or empty;
        at least one dispensing sensor to determine whether an unusually large amount of condiment has been continually dispensed; and
        a shutoff valve configured to prevent condiment dumping if the dispensing sensor determines that an unusually large amount of condiment has been continually dispensed, wherein the shutoff valve is only reset to allow normal operation of the apparatus upon receiving an input instruction to reset the shutoff valve.

2. The touch-less automatic condiment dispenser of claim 1 further comprising:
    at least a second condiment containing compartment,
    at least a second dispenser,
    at least a second dispensing sensor; and
    at least a second condiment level sensor.

3. The touch-less automatic condiment dispenser of claim 1 wherein the apparatus further comprises a control panel with mobile app capabilities.

4. The touch-less automatic condiment dispenser of claim 3 wherein the mobile app is configured to control the type of condiment to be dispensed and the volume of condiment to be dispensed.

5. The touch-less automatic condiment dispenser of claim 3, wherein the indication comprises sending an alert to the mobile app to alert that the at least one condiment is low or empty.

6. The touch-less automatic condiment dispenser of claim 1 wherein the apparatus further comprises UV lighting elements for sanitizing the dispensing elements.

7. The touch-less automatic condiment dispenser of claim 1 wherein the apparatus further comprises heating and/or cooling elements that can be configured to maintain individual condiment packages within the apparatus at specific temperatures.

8. The touch-less automatic condiment dispenser of claim 1, further comprising a handle at a top of the housing.

9. The touch-less automatic condiment dispenser of claim 1 wherein hands-free operation comprises dispensing the at least one condiment in response to a hand gesture by a user in front of the at least one dispensing sensor.

10. The touch-less automatic condiment dispenser of claim 1, wherein the indication comprises actuating an indicator light to alert that the at least one condiment is low or empty.

11. The touch-less automatic condiment dispenser of claim 1 wherein the shutoff valve is configured to allow for resetting via a control panel.

12. The touch-less automatic condiment dispenser of claim 1 wherein the shutoff valve is configured to allow for resetting via a mobile app.

13. The touch-less automatic condiment dispenser of claim 1, wherein the apparatus further comprises at least one of a napkin holder or a utensils holder.

14. The touch-less automatic condiment dispenser of claim 1, wherein the apparatus is mounted on a pedestal stand.

15. A method for operating a condiment dispenser via a mobile app, the method comprising:
    inputting commands via the mobile app to dispense a condiment from the dispenser;
    inputting commands via the mobile app for dispensing a specific volume of the condiment;
    dispensing the condiment according to the specific volume;
    detecting via a dispensing sensor that an unusually large amount of the condiment has been continually dispensed from the dispenser;
    actuating a shutoff valve within the dispenser to prevent further dispensing of the condiment upon detection than an usually large amount of the condiment has been continually dispensed from the dispenser; and
    resetting the shutoff valve to return the dispenser to normal operation.

16. The method of claim 15, wherein the method further comprises:
    detecting via a condiment level sensor that at least one condiment is low or empty; and
    providing an indication that the at least one condiment is low or empty.

17. The method of claim 16, wherein the providing an indication comprises transmitting an alert to the mobile app that the at least one condiment is low or empty.

18. The method of claim 16, wherein the providing an indication comprises actuating an indicator light disposed on the dispenser to indicate that the at least one condiment is low or empty.

* * * * *